(12) United States Patent
Handly

(10) Patent No.: US 7,442,340 B2
(45) Date of Patent: Oct. 28, 2008

(54) CHEMICAL AGENT MONITORING SYSTEM

(76) Inventor: Robert Handly, 6732 Mayard, Houston, TX (US) 77041

( * ) Notice: Subject to any disclaimer, the term of this patent is extended or adjusted under 35 U.S.C. 154(b) by 563 days.

(21) Appl. No.: 10/368,204

(22) Filed: Feb. 18, 2003

(65) Prior Publication Data

US 2004/0161856 A1 Aug. 19, 2004

(51) Int. Cl.
*G01N 30/00* (2006.01)

(52) U.S. Cl. .............................. 422/83; 422/88; 436/104

(58) Field of Classification Search .................... 422/83, 422/88; 436/104
See application file for complete search history.

(56) References Cited

U.S. PATENT DOCUMENTS

| | | | | |
|---|---|---|---|---|
| 3,844,905 A | * | 10/1974 | Epstein et al. ........... | 205/785.5 |
| 4,048,022 A | * | 9/1977 | Epstein et al. ........... | 205/785.5 |
| 4,272,479 A | * | 6/1981 | Huneke et al. ................ | 422/57 |
| 4,542,641 A | * | 9/1985 | Eyler ......................... | 73/31.07 |
| 2003/0180179 A1 | * | 9/2003 | Rosenbaum .................... | 422/4 |

* cited by examiner

*Primary Examiner*—Lyle A Alexander
(74) *Attorney, Agent, or Firm*—Walter R. Brookhart; Shook, Hardy & Bacon LLP

(57) ABSTRACT

A method and apparatus for sampling for the chemical warfare agent VX, where it is advantageous for the VX to be converted to its G-analog to facilitate aspirator induced movement of the sample through a sample line, to a sampling tube or to sample detection apparatus. A conversion tube assembly has a conversion tube member defining inlet and outlet openings and having a conversion filter therein, which is saturated with an A to G reagent for a chemical warfare agent of interest. The conversion filter assembly includes non-impregnated filter elements and the ends thereof and is retained in position intermediate to the ends of the conversion tube member by retainer elements, which may be tubes or rings. The conversion filter assembly is adapted to be received by a compression fitting or may be directly assembled to a sampling tube or sampling line.

20 Claims, 3 Drawing Sheets

CHEMICAL AGENT MONITORING SYSTEM

BACKGROUND OF THE INVENTION

1. Field of the Invention

This invention relates generally to the detection, identification and quantification of the chemical warfare agent commonly referred to as "VX",(methylphosphonothioic acid, having the chemical formula, [O-ethyl S-(2-diisopropylaminoethyl) methyl phosphonothiolate]). More particularly, the present invention concerns air monitoring systems that facilitate detection of the chemical warfare agent VX by converting VX into its G Analog, which is easier to detect and works more efficiently with systems that are currently in use in many disciplines of chemical warfare agent detection, identification and quantification. Even more specifically, the present invention concerns improved sampling and analytical apparatus and methods to be used in or near chemical warfare agent manufacturing or handling facilities, in or near chemical warfare agent demilitarization facilities, at perimeter sampling sites strategically located near such facilities, and at battlefields or any environments where chemical warfare agents may be present. The present invention has applications in a wide variety of situations, including challenge testing for gas chromatographs to facilitate the monitoring or testing for gases, liquids and residues of VX as well as other similar chemical warfare agents.

2. Description of the Prior Art

Nerve agents are chemical compounds, which affect the central nervous system of animal life. These nerve agent compounds were originally derived from pesticide development work originally done in Germany. The physiological effect of nerve agents in man and other animal life is the interruption of nerve impulses along the central nervous system, thus disturbing essential body functions, such as breathing, vision and muscular control, and potentially causing death. As mentioned above, the principal nerve agent of interest from the standpoint of chemical warfare agent detection according to the present invention is "VX", (methylphosphonothioic acid, having the chemical formula, [O-ethyl S-(2-diisopropylaminoethyl) methyl phosphonothiolate]). Though the present invention is described in detail here, particularly as it relates to detection and quantification of the nerve agent VX, it is to be borne in mind that it is not intended that the present invention be restricted solely to its association with the nerve agent VX, but rather that the present invention be applicable to facilitate simple, efficient and low cost sampling for the presence of any similar chemical warfare agent or compound with which the present invention is capable of effective use. For example, under certain circumstances the present invention will find effective use for achieving samples of other nerve agents, particularly "GB" and "HD" as well as other nerve agents and chemical warfare agents that are not currently known in detail in the United States. Thus, when the agent "VX" is mentioned herein, it is intended that the present invention will be applicable to the agent VX and to any other nerve agent or chemical warfare agent that may be utilized in chemical warfare. Other chemical warfare agents of interest from the standpoint of the present invention are Phosphonothioic acid, methyl-, S-(2-bis(1-methylethylamino)ethyl) 0-ethyl ester O-ethyl; S-(2-diisopropylaminoethyl) methylphosphonothiolate; S-2-Diisopropylaminoethyl O-ethyl methylphosphonothioate; S-2((2-Diisopropylamino)ethyl) O-ethyl methylphosphonothiolate; O-ethyl S-(2-diisopropylaminoethyl) methylphosphonothioate; O-ethyl S-(2-diisopropylaminoethyl) methylthiolphosphonoate; S-(2-diisopropylaminoethyl) o-ethyl methyl phosphonothiolate; Ethyl-S-dimethylaminoethyl methylphosphonothiolate VX EA 1701; and TX60

The nerve agent "VX" acts on the body by inhibiting the enzyme cholinesterase. When this enzyme is prevented from working, nerves react uncontrollably, interrupting essential body functions such as breathing, vision and muscular control, and potentially causing death. The principal route of exposure to "VX" is via absorption through the skin, though it can also be absorbed by the digestive tract or by the respiratory tract if in vapor or aerosol form.

In the past 5 years, new methods and systems for monitoring chemical warfare agents have increased, and many of the methods and systems require taking air samples from a given location or environment and transporting the air sample through sample lines and into an adsorbent tube, known as a Depot Area Air Monitoring System tube (DAAMS tube), for later analysis, or directly onto a suitable type of chemical detector, such as a surface acoustic wave detector, a gas chromatograph or any number of other detectors often associated with but not limited to chromatography. The US Government is currently destroying its chemical weapons stockpiles in specified demilitarization plants, and stringent safety standards are imposed on all operations involving chemical warfare agents. These safety standards are intended to protect the demilitarization plant workers and also to protect the general public from accidental exposure to harmful levels of chemical warfare agents. Adequate chemical analysis procedures for the determination of the presence of chemical warfare agents in work areas, in the perimeter air of chemical warfare agent handling facilities and in the various plant effluents of such facilities are critical aspects of the U.S. Government's safety program. Samples of work area and perimeter air surrounding a chemical warfare handling facility area and samples of various effluents (gases, liquids, and solids) must be regularly and routinely collected and analyzed to certify that they do not contain chemical warfare agents at concentrations exceeding the limits established by the US Surgeon General. Chemical warfare agents are becoming an increasing worldwide concern, and in many different countries both military and civilian agencies and communities are beginning to do independent chemical agent analysis of their environments to detect and identify the presence of chemical warfare agents and the source or origin thereof. More specifically, these countries, including the United States, have initiated monitoring for chemical warfare agents for the safety of their communities. The analytical methods currently used by the U.S. Government for the determination of trace quantities of VX generally comprise air monitoring by collecting samples of atmospheric or stack-gases.

According to the basic methodology for the Depot Area Air Monitoring System (DAAMS) determination of VX, because the gas-chromatographic determination of trace quantities of VX is not a straightforward matter, agent VX is converted to its G-analog (ethyl methylphosphonofluoridate) before it is collected for analysis according to DAAMS procedures. Conversion of agent VX to its G-analog is accomplished by passing the sample (gas, liquid, solid or combination thereof) through an $AgNO_3/KF$-impregnated polyester filter (V-to-G conversion filter) connected to the inlet end of the sorbent tube. The conversion of VX to its G-analog can be illustrated by the following reaction:

$$CH_3CH_2O-P(=O)(CH_3)-SCH_2CH_2N-(C_3H_7)_2 + Ag^+F^- \longrightarrow$$

$$CH_3CH_2O-P(=O)(CH_3)-F + Ag-SCH_2CH_2N-(C_3H_7)_2$$

Chemical warfare agent sampling apparatus has been developed using a fitting which is intended for releasable mounting of $AgNO_3$/KF impregnated filter elements or circles through which environmental air is drawn for conversion of any VX chemical warfare agent content to its G-analog. To ensure the functionality of a gas chromatograph, the conversion filters are frequently challenged with a solution having a known quantity of the chemical warfare agent VX, which is converted to its G-analog and then conducted to the detector of a gas chromatograph, where it is detected and quantified. It has been determined that conversion filters for the determination of VX as its G-analog function quite well when prepared by impregnating a typically non-woven fibrous material with $AgNO_3$/KF. A backup filter of the same or different fibrous filter material in non-impregnated form has been located at the downstream end of the impregnated filter material in order to prevent flakes of the conversion reagent from being swept from the conversion filter into the sampling tube or apparatus along with the air being drawn through the conversion filters by the vacuum source that is typically used. In the past, as shown in FIG. 9, and identified as "Prior Art", conversion filters, impregnated with $AgNO_3$/KF, for conversion of VX were inserted into a compression fitting, typically at the inlet end and secured by a ferrule and nut assembly of the fitting. This was a difficult and time-consuming task, since the conversion filters are quite small, being in the order of from about 3/16 inch to about 1 inch in diameter and having a thickness in the order of about 1/16 inch, and also because the worker's hands may be gloved and protective garments may be worn, especially if the presence of VX is known or suspected. The conversion filter assembly, including the impregnated and non-impregnated filter substrates, were then secured within the fitting with the compression nut at the inlet of the fitting. If the conversion filter assembly is to be removed for replacement, the compression nut and ferrule assembly must be removed and the small filter elements are typically manually removed from the fitting. Thus, filter replacement has been a time-consuming and labor intensive process, adding significantly to the time, cost and difficulty of the chemical warfare agent testing process.

With a conversion filter assembly in place, the converted G analog of the VX in the sample is then conducted to a DAAMS tube, to a gas chromatograph or to any other sample detection and measurement system that is being utilized.

It is necessary to effect formal compliance with regulations concerning chemical warfare agent sampling procedures, including that the parameters of each sample, such as lot number, date of preparation, date of installation, date of removal, identity of specific constituents, etc. be recorded, so that controlled identification and tracking of chemical warfare agent samples can be accomplished. According to sampling procedures presently in use, the conversion filters and backup filters cannot be labeled. Thus, they must be placed in special containers that can be labeled and placed in a tracking system. In sum, there is the possibility for significant error in labeling and component identification that complicates and enhances the cost, as well as influencing the reliability of the chemical warfare agent sampling procedure. Therefore, it is desirable to provide a chemical warfare agent sampling procedure that efficiently facilitates labeling and tracking of samples.

SUMMARY OF THE INVENTION

A principal objective of the present invention is to develop improved sampling and analytical methods to be used at demilitarization plants both in the U.S. and abroad and at any site where there is suspected use, storage or production facilities for chemical warfare agents or for monitoring gases, liquids, and residues for the agent VX.

It is another important feature of the present invention to provide a novel method and apparatus for simple and commercially efficient conversion of VX into its G-analog in order to facilitate the collection of environmental samples of chemical warfare agents;

It is another feature of the present invention to provide a novel tubular apparatus which is easily installed to and removed from the inlet end of a sample line, fitting or apparatus and which contains an AgF impregnated filter material, thus eliminating the need for manual installation and removal of individual AgF pads from compression type filter support fittings or the like;

It is another feature of the present invention to provide a novel tubular conversion filter apparatus having a reagent saturated filter or filter assembly located therein and which may be simply, efficiently and safely challenged with a dilute solution containing a known quantity of a chemical warfare agent, thus permitting efficient use of the conversion filter apparatus for challenging a gas chromatograph or any other suitable type of detector for chemical warfare agents;

It is also a feature of the present invention to provide a novel chemical warfare agent conversion tube which is applicable for use in chemical warfare agent facilities, demilitarization facilities, perimeter chemical warfare agent monitoring apparatus and portable chemical warfare agent monitoring apparatus;

It is an even further feature of the present invention to provide a novel conversion filter assembly, which permits workers to quickly and efficiently effect installation and/or removal of conversion filter apparatus to facilitate efficient and low cost monitoring procedures for chemical warfare agents.

Briefly, according to the principles of the present invention, a chemical warfare agent conversion filter assembly is provided, having a conversion tube, with a conversion filter of desired length or dimension located therein. The conversion filter is typically composed of a plurality of circles of non-woven polyester material that are placed in stacked form within a tubular member so as to define a filter stack of desired length or height. The filter stack is saturated with $AgNO_3$/KF either prior to insertion into the conversion tube or, in the alternative, can be saturated in place within the conversion tube. If desired, one or more non-impregnated filter circles may be in abutment with one or both ends of the impregnated filter stack in order to assist in securing the filter stack in place and to prevent reagent particulate from being swept into the sampling tube by the vacuum induced air flow that occurs during sampling. One or more retainer elements, which may be composed of smaller diameter tubular members or retainer rings, may be fixed in any suitable manner within the conversion tube with ends thereof in retaining engagement with the filter stack or the non-impregnated filter elements at the ends of the filter stack. These retainer elements assist in maintaining the filter stack properly located between the inlet and outlet ends of the conversion tube and in preventing its movement within the conversion tube during handling, shipping and use.

A conversion filter assembly of the type briefly described above may be used in a number of different sampling combinations. For example, a conversion filter may be received and supported by a conventional compression fitting with its inlet opening exposed to an environment being sampled and its outlet end in communication with the flow passage of the fitting. The outlet of the compression fitting may be in communication with a sample line leading to a DAAMS tube bank or may be coupled directly with a DAAMS tube. As another example, a conversion filter may have its outlet end received in sealed relation by a sampling line leading to a DAAMS filter bank that may be located some distance away from the conversion filter. Also, if desired, a sampling line may be located in sealed relation within the outlet end of the conversion filter. As an even further alternative, the outlet end of a conversion filter may be received in sealed assembly with the inlet end of a DAAMS sampling tube. The outlet end of a conversion filter may be arranged to convey the converted sample directly to a gas chromatograph or to any other suitable instrument for detection and quantification of the G-analog of VX or any similar chemical warfare agent.

When a compression fitting is used for connection with a V to G conversion filter assembly, with the inlet compression nut loosened, the outlet end of the conversion tube is simply inserted through the inlet opening of the inlet compression nut and is extended into the opening of the compression ferrule of the compression fitting. Thereafter, the compression nut is tightened sufficiently to cause the compression ferrule to establish frictional gripping and sealing with the conversion tube. The outlet end of the tubular compression fitting, or other sampling tube support fitting, is secured to the inlet end of a sampling line or apparatus having a sampling opening or passage. The sampling line is in communication with an aspirator, i.e., vacuum pump, which draws environmental media, including gas, liquid and solid reagent residue particulate from an area or environment of interest through one or more DAAMS tubes. The vacuum of the aspirator may act on a sampling tube assembly, an Automatic Continuous Air Monitoring System (ACAMS), or on a Hapsite or SAW, depending on the sampling arrangement that is selected.

The sampling tube assembly has a sample detection tube within which is located a quantity of an adsorbent material such as Chromosorb™, HayeSep™ or Tenax™. The adsorbent material may be located alone within the sampling tube assembly if desired. In the alternative, and perhaps preferably, backup pads or circles composed of any suitable fibrous material are located in contact with each end of the adsorbent material to secure it in place and to prevent any solid constituents of the adsorbent material from being drawn out of the sampling tube by vacuum induced air, gas or other fluid flow. Inner tubular members or other suitable retainer elements can be located within the outer tubular member of the sampling tube assembly and engage the backup filter pads, thus securing them at locations intermediate to the length of the sampling tube member.

By using the present invention, when changing of conversion tubes is appropriate, it will not be necessary for a worker to handle any small objects, such as conversion filter pads, backup filter circles or the line; thus, the work can be carried out fairly rapidly even though the worker may be wearing protective gloves as well as protective garments. If a compression fitting is employed for retention of a conversion tube assembly, installation of the conversion tube assembly is accomplished simply by inserting the outlet end of a replacement conversion tube through the opening of a compression nut and through the opening of a friction retention ferrule. When a replacement conversion tube assembly has been properly located within the compression fitting, a worker will tighten the compression nut, causing the tapered friction retention ferrule to be deformed so that it establishes a tight gripping and sealing relation with the outer tubular member of the conversion tube assembly. This conversion tube replacement procedure will take only a few seconds, thereby minimizing the labor cost of conversion tube replacement.

As explained above, it is desirable to provide means for labeling each conversion tube assembly so that its parameters of composition, its date of manufacture, date of use, and any other desirable information can be efficiently identified and tracked according to regulations. In the past, this has not been practical since the reagent saturated conversion pads were manually installed within fitting assemblies and manually removed from the fitting assemblies for replacement. According to the present invention, identification tags are applied to the tubular members of the conversion tube assemblies, thus providing identification information, such as lot number, date and time of assembly and permitting installation and removal information to be written or printed on the identification tags. The conversion tube components are permanently retained within the conversion tube assembly and the identification tags are permanently affixed to the outer tubular member of the conversion tube assemblies. This feature facilitates ease of tracking of the conversion tubes throughout the various stages of processing and utilization. Additionally, the identification tags can be provided with bar codes to enable laser scanning for automated identification and tracking of each conversion tube assembly.

BRIEF DESCRIPTION OF THE DRAWINGS

So that the manner in which the above recited feature, advantages and objects of the present invention are attained and can be understood in detail, a more particular description of the invention, briefly summarized above, may be had by reference to the preferred embodiment thereof which is illustrated in the appended drawings, which drawings are incorporated as a part hereof.

It is to be noted, however, that the appended drawings illustrate only a typical embodiment of this invention and are therefore not to be considered limiting of its scope, for the invention may admit to other equally effective embodiments.

In the Drawings:

FIG. 1 is a plan view of a chemical warfare agent sampling assembly having a connection fitting such as a compression fitting with a chemical warfare agent conversion tube assembly connected at the inlet end of the fitting and a sampling tube assembly connected at the outlet end of the fitting;

FIG. 2 is a longitudinal sectional view showing a chemical warfare agent conversion tube assembly embodying the principles of the present invention and representing the preferred embodiment of the invention;

FIG. 3 is a longitudinal sectional view showing a chemical warfare agent conversion tube assembly embodying the principles of the present invention and representing an alternative embodiment of the invention;

FIG. 4 is a longitudinal sectional view showing a chemical warfare agent conversion tube assembly embodying the principles of the present invention and representing a further alternative embodiment of the invention;

FIG. 5 is a longitudinal sectional view showing a chemical warfare agent conversion tube assembly according to the present invention, having a tubular element of smaller dimension received within the outlet end thereof, the smaller tubular element being a sample tube, a sample conducting line or a connecting line to a suitable detector;

Figure 8:
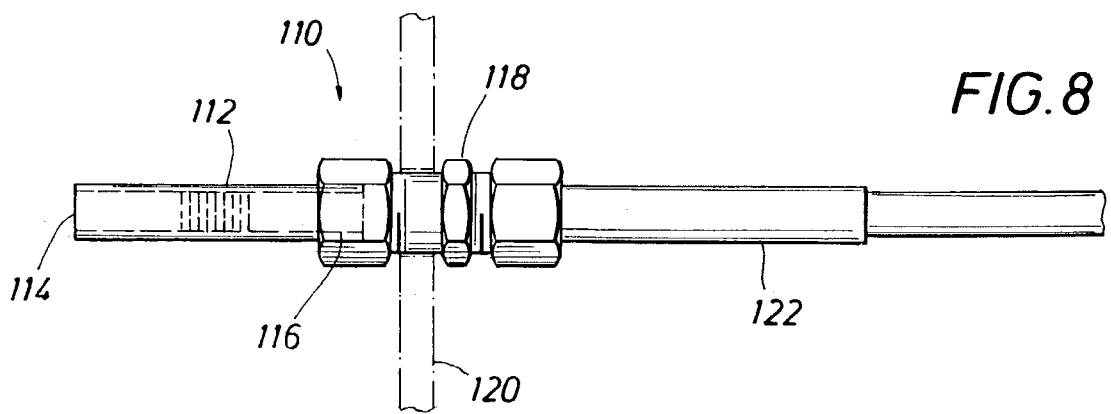
Figure 9A:
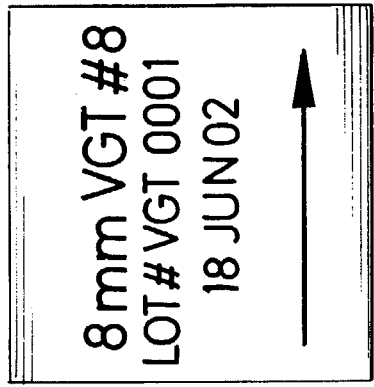
Figure 9:
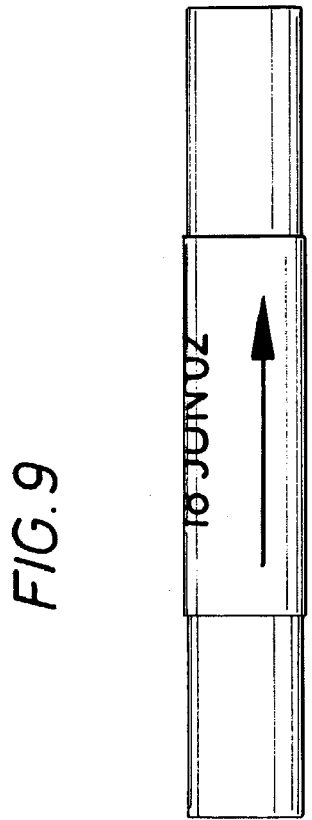
Figure 10:
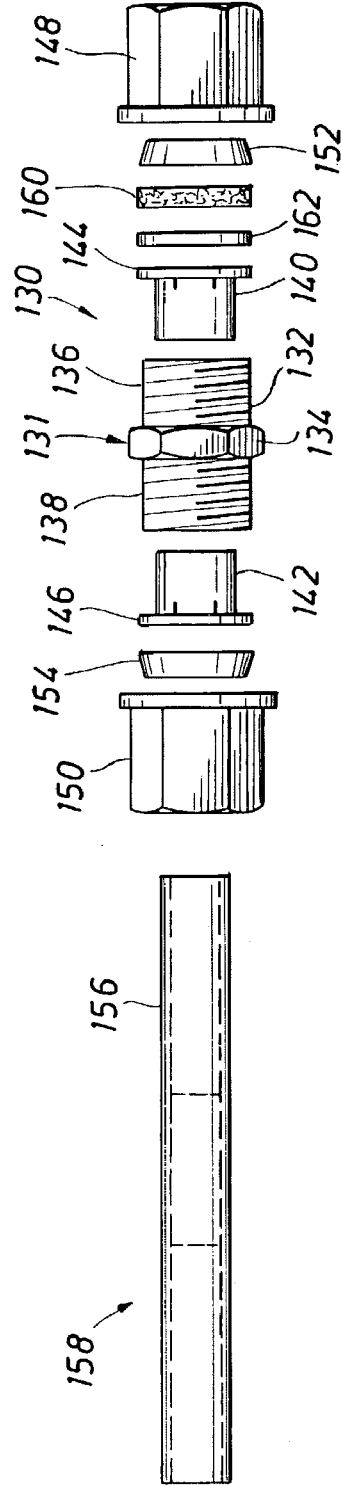

FIG. 8 is a partial longitudinal elevational view showing a chemical warfare agent conversion tube assembly embodying the principles of the present invention being in connection with the inlet end of a connection fitting and with the assembly having a sample conducting tube connected with the outlet end of the fitting and leading to a detector, sample collection tube or sample collection system for the converted analog of the chemical warfare agent of interest;

FIG. 9 is an elevational illustration showing the conversion tube assembly of the present invention, with an identification and tracking label secured to the conversion tube member, thus enabling identification and tracking of conversion tube assemblies;

FIG. 9A is an illustration showing an identification and tracking label prior to its attachment to the conversion tube member; and FIG. 10 is an exploded view showing a tubular fitting identified as "prior art" which has been used in the past for supporting one or more reagent saturated conversion pads and non-saturated filter pads and being shown with a sample line being connected at the outlet end of the fitting for conducting sample flow to a DAAMS sample tube or sample tube bank.

DETAILED DESCRIPTION OF PREFERRED EMBODIMENT

Figure 1:
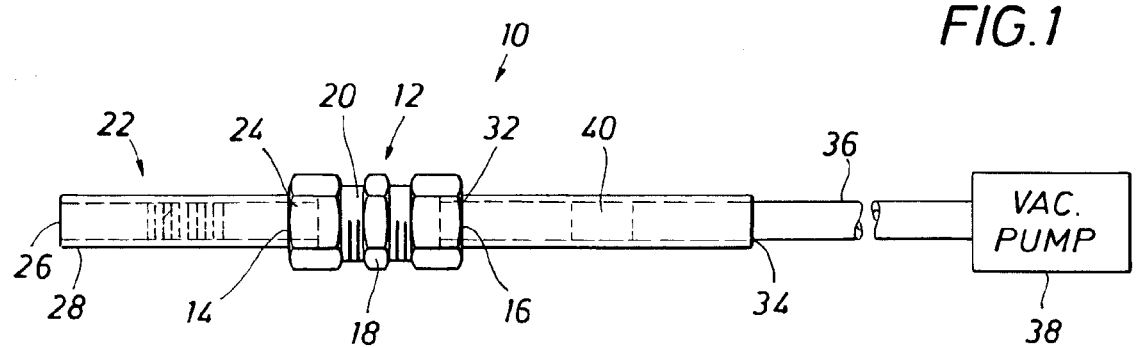

Referring now to the drawings and first to FIG. 1, in the partial longitudinal sectional view there is shown, generally at 10, a chemical warfare agent sampling assembly that is constructed according to the principles of the present invention. The sampling assembly shown includes a fitting member 12, which may be a compression fitting that may be of the type shown in the exploded view of FIG. 9. The compression fitting has an inlet end 14 and an outlet end 16, each having openings and has a central body 18 defining a flow passage 20. The compression fitting has nut and compression ferrule assemblies at each of its inlet and outlet ends for establishing frictional clamping and sealing relation with tubular elements.

Figure 2:
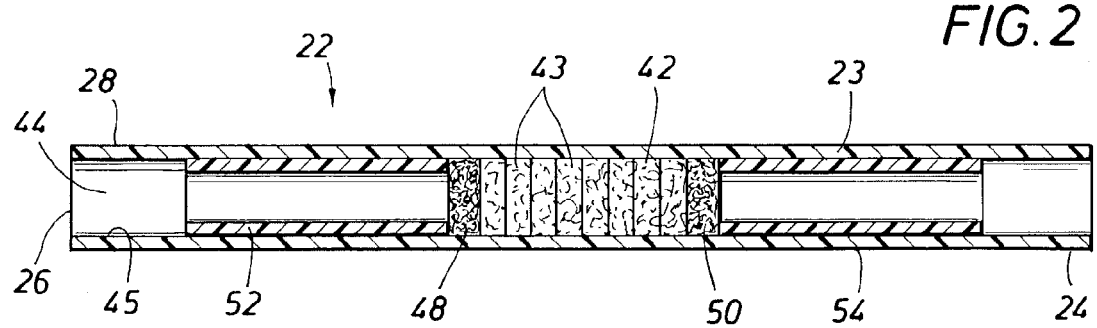

A conversion tube assembly shown generally at 22, and preferably being of the form shown in the longitudinal sectional view of FIG. 2, has its outlet end 24 secured in sealed and retained assembly with the fitting 12 and with an opening 26 at the inlet end 28 thereof exposed to an environment for which air sampling is desired for determination of the presence, if any, of the chemical warfare agent VX or another agent of interest. A DAAMS sampling tube 30 is shown with its inlet end 32 received in connected and sealed relation with the outlet end 16 of the fitting 12 and with its outlet end 34 being connected with a sample line 36, which communicates with a vacuum pump 38 to provide the motive aspiration force for drawing samples of the selected environment through the conversion tube 22, the fitting 12 and the sampling tube 30 or a bank of like sample tubes. Each of the sample tubes is typically composed of Pyrex™ glass tubing or polymer tubing and will have located therein a sorbent filter 40 composed of a fibrous polymer material. Typically, each end of the sorbent filter will be backed up by a glass wool filter or any other suitable filter and support that assists in containing the sorbent filter within the tubing and ensuring that sample particulate is not drawn into the aspirator 38.

Figure 3:
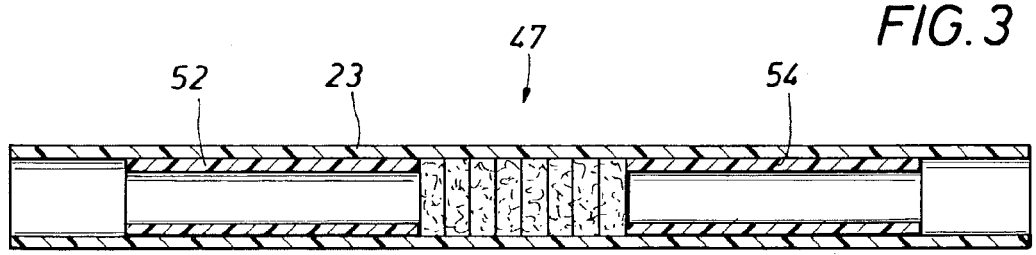

A conversion tube assembly, shown generally at 22, has a conversion filter 42 located within the internal passage 44 defined by an internal cylindrical surface 45 of the tubular member 23 and located intermediate the ends of the internal passage. The conversion filter 42 is typically composed of a plurality of relatively thin circular non-woven fibrous filter pads or circles 46 that are positioned in contact with one another so as to form a filter stack defining the conversion filter. The filter pads 46 of the filter stack are saturated with or contain a conversion reagent for the chemical warfare agent of interest. In the case of the chemical warfare agent VX, for example, the conversion reagent will take the form of $AgNO_3$/KF. One or more non-saturated back-up filter elements 48 and 50 are located within the internal passage 44 of the tubular member 23 and engage respective ends of the filter stack. The backup filters serve to retain the filter stack in place within the passage 44 and to prevent any flakes or particulate of the reagent from being swept into or toward a sampling tube assembly or sampling tube bank by air flow under the influence of the vacuum source of the aspirator. To retain the back-up filter elements in place, a pair of retainer elements 52 and 54, are located within the internal passage 44 of the tubular member 23 and provide retaining contact with the backup filter pads or the ends of the conversion filter stack. As shown in FIGS. 2 and 3, the retainer elements 52 and 54 may take the form of elongate inner tubular members composed of the same or similar material as the tubular member 23. The inner tubular members 52 and 54 are preferably sized to establish a friction fit with the inner cylindrical surface 45 of the flow passage 44 of the tubular member 23. If desired, the inner tubular members may be permanently affixed and sealed within the tubular member 23, such as by bonding, cementing, heat welding, chemical welding or the like.

An alternative embodiment of the conversion filter assembly is shown generally at 47 in FIG. 3, which differs from the conversion filter assembly 22 of FIG. 2 only in that the inner tubular members 52 and 54 directly contact the ends of the filter stack. In this case, no back-up filter elements are shown to be employed at the ends of the filter stack.

A further alternative embodiment of the conversion filter assembly is shown generally at 56 in FIG. 3 and embodies a tubular member 58 that may be of the same dimension and may be composed of the same material or range of materials, as compared with the tubular member 23 of FIGS. 2 and 3. The tubular member 58 defines an inner cylindrical surface 60 that defines the flow passage 62 of the tubular member. A body or bed 64 composed of conversion reagent-saturated, preferably non-woven, fibrous material is located within the flow passage 62, intermediate the inlet and outlet ends 66 and 68 of the tubular member 58. To secure the body or bed 64 in place, a pair of back-up filter elements 70 and 72 are located in contact with respective ends thereof. The back-up filters, which are typically composed of a non-saturated, non-woven fibrous material, such as polyester felt, are retained within the tubular member 58 by retainer elements or rings 74 and 76. The retainer elements or rings 74 and 76 may be secured within the internal cylindrical surface 60 by friction fit if desired, or may be bonded, welded or otherwise fixed to the inner cylindrical surface 60. These retainer rings may be internally tapered as shown, may be of simple cylindrical shape or may take any other suitable geometric form without departing from the spirit and scope of the present invention.

Figure 4:
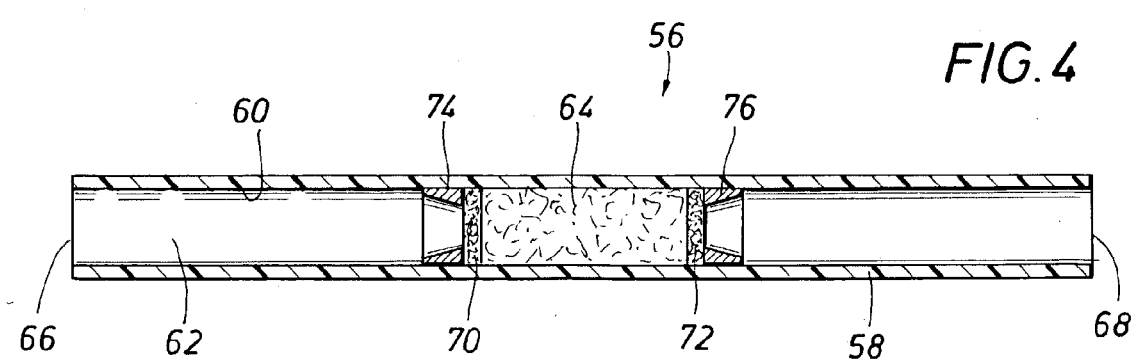
Figure 5:
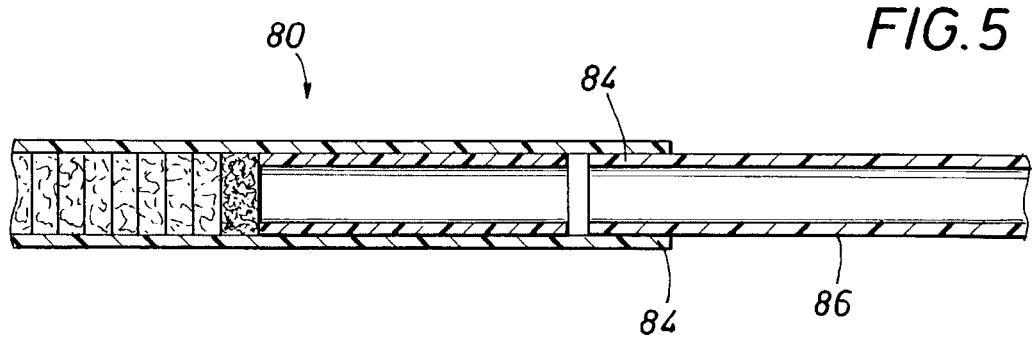
Figure 6:
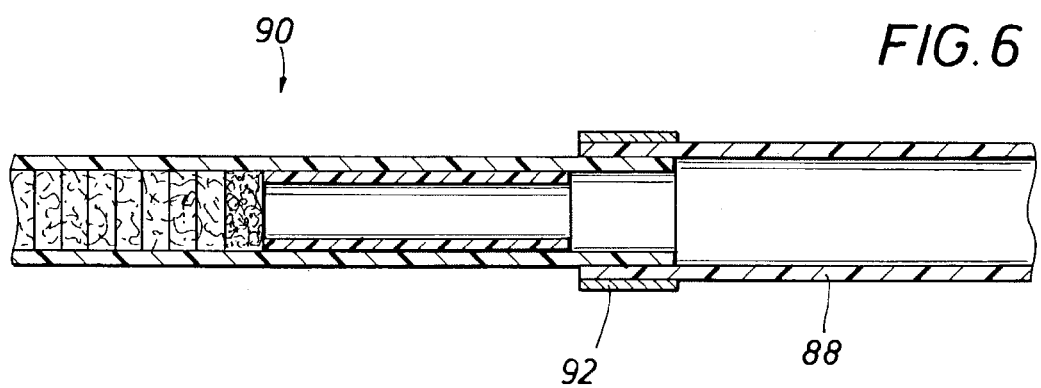
FIG. 6 is a longitudinal sectional view showing a chemical warfare agent conversion tube assembly having the outlet end thereof received within the inlet end of a tubular element, which may be a sample line, a sample tube or a conducting line leading to a detector.

According to the embodiment of FIG. 5, a conversion tube assembly shown generally at 80, and which may be of the type shown in either of FIG. 2, 3 or 4, has an outlet end 82 of a dimension for receiving the inlet end 84 of a sample tube 86 in friction fitting sealed relation. The sample tube 86 can be of a sufficiently small external diameter as to establish a close, friction-type fit within the outlet end of the conversion tube assembly. Also, if desired, the sample tube and the outlet end of the conversion tube assembly may be secured in assembly by any other suitable means, including clamping by any suitable clamp element. It should be borne in mind that the connection between the conversion tube assembly and the sample tube will be separated when it is desired to replace the conversion tube assembly. As shown by the embodiment of FIG. 6, the sample tube 88 may be of larger diameter than the outer diameter of the conversion tube assembly 90, thereby permitting the inlet end of the sample tube to be positioned over the outlet end of the conversion tube assembly and secured by friction fit, by a clamp 92 or by any other suitable means.

Figure 7:
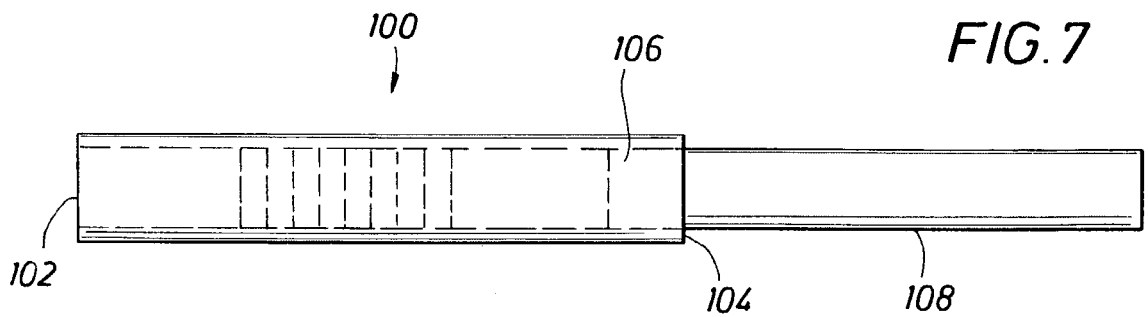
FIG. 7 is a longitudinal elevational view showing a chemical warfare agent conversion tube assembly according to the present invention, being connected directly to a chemical warfare agent sampling tube assembly and showing internal components thereof in broken line.

With reference now to the embodiment of FIG. 7, a conversion tube assembly, shown generally at 100, and which may take the form shown in FIGS. 1-4, is arranged with its inlet end 102 exposed to an environment to be sampled and its outlet end 104 coupled directly with the inlet end 106 of a sample tube assembly 108. The connection of the conversion tube assembly and the sample tube assembly may be maintained by a friction fit if desired, or may be retained by a clamp element as shown at 92 in FIG. 6 to permit separation of the conversion tube assembly and the sample tube assembly when desired.

Another embodiment of the present invention is shown generally at 110 in FIG. 7, wherein a conversion tube assembly 112 is shown to be positioned with its inlet end 114 exposed to an environment to be sampled and its outlet end 116 retained in assembly with a compression fitting 118. The compression fitting 118 may be located within an aperture of a wall structure as shown in broken line at 120, which may be the wall of a demilitarization facility, a wall of a perimeter sampling housing or monitoring station or the wall of any other structure that separates an area being sampled from an area to which the converted sample is conducted for collection and analysis. The compression fitting 118 is shown with its outlet connection in assembly with a sample line 122, which conducts the converted sample to an ACAMS or DAAMS station or to a gas chromatograph, or any other suitable detector.

With reference to FIGS. 9 and 9A, a conversion tube assembly such as that shown at 22 in FIGS. 1 and 2, is provided with an identification and tracking label 123 which is used to specifically identify each conversion tube assembly and enable its efficient and low-cost tracking from the time of its manufacture, through its date and time of use and to enable its identification and tracking during storage after it has been used. In addition to printed identification material, the label 123 may also be provided in a form on which use and tracking data may be written. The label 123 may also be provided with a laser readable bar code to enable computerized identification and tracking of conversion tube assemblies. This feature enables users of the present invention to easily comply with regulations requiring identification and tracking of components that are utilized for chemical warfare agent monitoring.

Referring to the exploded view of FIG. 10, a chemical warfare agent sample conversion and sampling system is shown generally at 130 which represents the prior art that has been utilized in the past. This sampling system incorporates a compression fitting, shown generally at 131, which includes a union member 132 that is composed of a suitable material such as metal, polypropylene, Teflon™ or other suitable polymer or fluoropolymer material. The union member 132 has an intermediate flange 134 of hexagonal configuration for receiving a standard wrench and is of tubular construction, defining an internal fluid flow passage and having threaded connections 136 and 138. A pair of ferrule members 140 and 142 have tubular sections that are received within the respective flow passage ends that are defined by the threaded connections 136 and 138 of the union member 132. The ferrule elements also have end flanges 144 and 146 of a dimension for abutting engagement with the circular ends of the union member. The ferrule elements are preferably composed of a deformable material such as polypropylene or a suitable metal, which is forced into sealed engagement with the circular ends of the union member by compression inducing nut elements 148 and 150 in a manner that is conventional and well-known for compression fittings. Tapered compression ferrule elements 152 and 154, which may also be composed of polypropylene, any other suitable polymer material or a suitable metal material are deformed by the compression inducing nut element 150 to establish a friction gripping relation with the inlet end of the tubular member 156 of a sample tube assembly shown generally at 158. The compression nut 150 is tightened on the threaded section 138 of the union 132 to cause the tapered compression ferrule 154 to establish a gripping, retaining and sealing relation with the outer tubular member of the sampling tube assembly 158.

As shown in the upper portion of FIG. 10, a conversion filter 160 and a backup filter 162 are positioned so as to be retained in assembly with the union 132 and ferrule 140 as the tapered ferrule 152 is tightened onto the union by the compression nut 148. If desired, two or more reagent saturated conversion filter elements may be retained by the compression nut and ferrule assembly. These conversion filter elements are installed by hand, typically by placing them in loose assembly with the compression nut and tapered ferrule and then screwing the compression nut onto the threaded section 136 of the union. The conversion filter is typically composed of a non-woven polyester material, which is typically die cut from a sheet or panel of the material. Prior to installation of the conversion filters, they will be saturated with one of the conversion reagents, e.g., $AgNO_3/KF$, depending on the chemistry of the chemical warfare agent of interest. The backup filter 162, which may be composed of non-woven polyester felt or any other suitable non-woven filter substrate, is positioned in abutting, supported relation with the end flange 144 of the ferrule 140 and provides support for the impregnated conversion filter or pad 160.

In the past a union member such as shown at 132 has been composed of a chemical resistant polymer material, such as polypropylene and the compression nuts and ferrules have been constructed of like material.

In view of the foregoing it is evident that the present invention is one well-adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the appended claims rather than the foregoing description, and all changes which come within the meaning and range of equivalence of the claims are therefore intended to be embraced therein.

I claim:

1. A chemical agent conversion tube assembly for use in a process for detecting an airborne chemical warfare agent comprising VX gas by drawing air to be analyzed for said agent through said assembly, comprising:
   a glass or polymer tube having an inlet and an outlet and defining a conversion passage therethrough,
   a chemical warfare agent conversion filter located within said conversion passage of said glass or polymer tube between said inlet and outlet, said chemical warfare agent conversion filter being sufficiently secured so as to prevent said chemical warfare agent conversion filter from being swept out of said glass or polymer tube due to said air flow through said glass or polymer tube, said chemical warfare agent conversion filter comprised of a plurality of adjacent filter elements defining a filter stack, and
   a conversion reagent disposed on at least some of said filter elements for converting said VX gas to a more volatile analog of said VX gas, said reagent producing said analog to be airborne whereby said plurality of filter elements within said conversion passage are sufficiently unrestricted to permit said analog to be carried by said air flow and to pass through said glass or polymer tube and through said outlet to a detection device located downstream of said chemical conversion tube for analysis of said analog from which the presence and concentration of VX gas in said air can be determined.

2. The chemical agent conversion tube assembly of claim 1, wherein said filter stack comprises three or more filter disks.

3. The chemical agent conversion tube assembly of claim 1, wherein at least one filter element on at least one side of said filter stack is non-saturated with said reagent.

4. The chemical agent conversion tube assembly of claim 1 wherein at least one retainer member is affixed inside of said glass or polymer tube in engagement with said conversion filter stack.

5. The chemical agent conversion tube assembly of claim 1, wherein said glass or polymer tube is sufficiently clear to permit visual verification that said chemical warfare agent conversion filter is positioned correctly and present within said glass or polymer tube.

6. The chemical agent conversion tube assembly of claim 1 further consisting of a label on an exterior surface of said glass or polymer tube to permit identification and tracking of said chemical warfare agent conversion filter.

7. A chemical agent conversion tube assembly for use in a process for detecting an airborne chemical warfare agent comprising VX gas by drawing air to be analyzed for said agent through said assembly, comprising:
   a polymeric conversion tube member having an inlet and an outlet and defining a conversion passage therethrough,
   a chemical warfare agent conversion filter located within said conversion passage of said conversion tube member, said conversion filter being comprised of a plurality of adjacent filter elements defining a filter stack, and
   a conversion reagent disposed on at least some of said filter elements for converting said VX gas to a more volatile analog of said VX gas, said reagent producing said analog to be airborne whereby said plurality of filter elements within said conversion passage are sufficiently unrestricted to permit said analog to be carried by said air flow and to pass through said glass or polymer tube and through said outlet to a detection device located downstream of said chemical conversion tube for analysis of said analog from which the presence and concentration of VX gas in said air can be determined.

8. The chemical agent conversion tube assembly of claim 7 wherein said filter stack comprises three or more filter disks.

9. The chemical agent conversion tube assembly of claim 7 wherein at least one filter element on at least one side of said filter stack is non-saturated with said reagent.

10. A conversion tube assembly for use in a system for detecting airborne VX gas by drawing air to be analyzed for said VX gas through said assembly, comprising:
    a polymeric, tubular member having an inlet and an outlet connected by a passageway through which air, possibly including said VX gas, can be drawn through said inlet, said tubular member being sufficiently large to permit easy handling and manipulation by one wearing gloves of the type typically associated with chemical warfare protective suits and being sufficiently large to accommodate an identification label on an exterior surface of said tubular member;
    a plurality of filter elements securely disposed adjacent one another within said passageway, each said filter element comprising an air permeable filter material;
    a conversion reagent comprising silver fluoride disposed on all of said filter elements except an element disposed nearest said outlet, said conversion reagent disposed for contact and capable of reacting with any said VX gas drawn through said inlet to convert said VX gas to its more volatile G analog which is readily swept from said passageway through said outlet by said air for downstream analysis for said G analog from which the presence and concentration of VX gas in said air can be determined; and
    an identification label affixed to said exterior of said tubular member, said label providing identification and tracking information concerning the manufacture and use of said assembly, said information presented in at least one format selected from pre-printed information, places for hand-written information and bar-coded information.

11. The conversion tube assembly of claim 10 wherein said tubular member is sufficiently clear to permit visual verification that said chemical warfare agent conversion filter is present and correctly positioned within tubular member.

12. A conversion tube assembly for use in a system for detecting an airborne chemical warfare agent comprising VX gas by drawing air to be analyzed for said chemical warfare agent through said assembly, comprising:
    a polymeric, tubular member having an inlet and an outlet connected by a passageway through which air, possibly including said chemical warfare agent, can be drawn through said inlet; and
    a conversion reagent dispersed upon a filter element securely disposed within said passageway, said conversion agent disposed for contact and capable of reacting with any said VX gas drawn through said inlet to quantitatively convert said chemical warfare agent to a more volatile analog which is readily swept from said passageway through said outlet by said air for downstream analysis for said analog from which the presence and concentration of VX gas in said air can be determined.

13. A conversion tube assembly for use in a system for detecting airborne VX gas by drawing air to be analyzed for said VX gas through said assembly, comprising:

a polymeric, tubular member having an inlet and an outlet connected by a passageway through which air, possibly including said VX gas, can be drawn through said inlet; and a conversion reagent comprising silver fluoride dispersed upon a filter element securely disposed within said passageway, said conversion reagent disposed for contact and capable of reacting with any said VX gas drawn through said inlet to convert said VX gas to its more volatile G analog which is readily swept from said passageway through said outlet by said air for downstream analysis for said G analog from which the presence and concentration of VX gas in said air can be determined.

14. The conversion tube assembly of claim 13 wherein said filter element comprises a fibrous material.

15. The conversion tube assembly of claim 13 wherein said filter element comprises at least one pad comprised of a fibrous, polyester material.

16. The conversion tube assembly of claim 15 further comprising a plurality of said filter pads disposed adjacent one another within said passageway and wherein a filter pad nearest said outlet is substantially free of said conversion agent.

17. The conversion tube assembly of claim 13 wherein said tubular member is sufficiently large to permit application of an identification label to the exterior thereof.

18. The conversion tube assembly of claim 17 further comprising an identification label affixed to the exterior of said tubular member, said label providing identification and tracking information concerning the manufacture and use of said assembly, said information presented in at least one format selected from pre-printed information, places for insertion of hand-written information and bar-coded information.

19. The conversion tube assembly of claim 13 wherein said tubular member is sufficiently transparent to allow visual confirmation of the presence of said conversion agent within said passageway.

20. The conversion tube assembly of claim 13 wherein said tubular member is sufficiently large to permit easy handling and manipulation by one wearing gloves of the type typically associated with chemical warfare protective suits.

* * * * *